(12) United States Patent  (10) Patent No.: US 8,097,021 B1
Kornel  (45) Date of Patent: Jan. 17, 2012

(54) PERCUTANEOUS SPINOUS PROCESS AND INTER-SPINOUS PROCESS STAPLER AND PLATE STABILIZING SYSTEMS

(76) Inventor: Ezriel E. Kornel, Bedford Hills, NY (US)

(*) Notice: Subject to any disclaimer, the term of this patent is extended or adjusted under 35 U.S.C. 154(b) by 1048 days.

(21) Appl. No.: 12/004,954

(22) Filed: Dec. 21, 2007

Related U.S. Application Data (60) Provisional application No. 60/876,946, filed on Dec. 22, 2006.

(51) Int. Cl.
*A61B 17/70* (2006.01)

(52) U.S. Cl. .................................. 606/248; 606/246

(58) Field of Classification Search .................. 606/60, 606/246, 248, 249
See application file for complete search history.

(56) References Cited

U.S. PATENT DOCUMENTS

| | | | | |
|---|---|---|---|---|
| 4,041,939 A | * | 8/1977 | Hall | 606/254 |
| 4,697,582 A | * | 10/1987 | William | 606/254 |
| 8,043,345 B2 | * | 10/2011 | Carl et al. | 606/279 |

* cited by examiner

*Primary Examiner* — Eduardo C Robert
*Assistant Examiner* — Ellen C Hammond
(74) *Attorney, Agent, or Firm* — Pryor Cashman LLP; Andrew S. Langsam (57) ABSTRACT

Spinous stabilizing system comprises spaced apart, pointed staples held to a connecting rod, a stabilizing plate and a set of locking caps for the staple's tips. The tips are forced through the spinous process and captured/secured by the locking caps, pulling the stabilizing plate against the spinous process and toward the heads of the staples and connecting rod. A pair of pliers loaded with the components on the lever arms can be squeezed together to cause the tips of the staple to penetrate the spinous processes and then become frictionally captured within the locking caps. The spacing between the staples are adjusted, pre-installation, by a locking screw acting on the connecting rod or, alternatively, after the device is percutaneously inserted, by laterally directed locking screws which mate with and cam a locking wedge. Matingly engageable speculated plates, installed by pliers, can also be used for spinous fixation.

12 Claims, 11 Drawing Sheets

PERCUTANEOUS SPINOUS PROCESS AND INTER-SPINOUS PROCESS STAPLER AND PLATE STABILIZING SYSTEMS

PRIORITY TO OTHER APPLICATIONS AND RELATED APPLICATIONS

This US patent application claims priority on U.S. provisional patent application Ser. No. 60/876,946, filed Dec. 22, 2006. The teachings, specification and drawings set forth in that US provisional patent application and the teachings, specification and drawings set forth in U.S. non-provisional patent application Ser. No. 11/650,096 filed Jan. 5, 2007 claiming priority itself on U.S. provisional patent application Ser. No. 60/756,711, filed Jan. 5, 2006 are herein incorporated by reference and their teachings are made a part hereof.

BACKGROUND OF THE INVENTION

The present invention relates to a novel system of true percutaneous spinous stabilization that allows for both spinous process immobilization as well as interspinous process distraction. In one embodiment the system comprises two or more staples or staple-like devices, each with a hole at their head ends and allowing for passage of a connecting rod therethrough. The connecting rod will serve to couple the two aligned yet spaced staples so that they act as a unit. A small locking screw is provided to lock the heads of the staples to the rod. A locking wedge can also be utilized for tightly securing the staples to the rod. In this embodiment, the small locking screws, when tightened into their respective holes in the heads of the staples, cam against the surface of the locking wedge and thereby lock the locking wedge (inside the head of the staples) securely against the common connecting rod. A cap (for accepting and securing the pointed ends of the staples, after they pass through the processes of the patient) and an end or stabilizing plate (to more uniformly distribute the forces of compression/contraction resulting from the staples acting on the end plate) serve to secure the staples at the desired locations.

The device can be percutaneously delivered and/or installed into the patient by use of a set of tools, i.e., a delivery system which allows for the delivery of the components in a relatively minimally invasive manner. As mentioned, the stabilizing plate rests against the spinous processes, on the opposite side from the staples' entry, and the plate via the locking caps secure the free ends of the staples to compress the spinal processes. The locking nuts are placed over the ends of the staples, on one side of the stabilizing plate to secure the entire construct in place and to keep the staples from backing out and/or becoming loose.

In one embodiment, a carrier and manually operable surgical like clamp, in the preferred form resembling a centrally linked or hinged pair of pliers, is provided to introduce the staples, connecting rod, stabilizing plate and locking caps or nuts into position about the spinal processes and to then allow the physician to manually compress the finger grips of the clamp to draw the staples (held together as a unit by the connecting rod) through the processes, and to clamp them through the stabilizing plate and into the locking caps or nuts. This then holds the unit together. One side of the clamp holds the staples, secured on the connecting rod by the small locking screws and/or the locking screws cooperating with the locking wedge to the connecting rod, and the other side or the opposing side of the clamp, the stabilizing plate and spaced locking nuts are held (spaced apart by the distance of the points of the staples held on the rod). As mentioned, a percutaneous delivery system (shown and described in non-provisional U.S. patent application Ser. No. 11/650,096 filed Jan. 5, 2007, claiming priority on U.S. Provisional Patent Application Ser. No. 60/756,711 filed Jan. 5, 2006, whose teachings, drawings and specification are incorporated by reference herein) can be employed with the stabilizing system described herein. That delivery system basically includes a delivery tube having a central working channel which ultimately (i.e., by sequentially using the other elements of that system) allows for the introduction of the carrier clamp, along with the associated hardware i.e., the staples, the connecting rod, the stabilizing plate and the locking caps, in a percutaneous manner. The present system also may include a screwdriver like device which is adapted to travel along the delivery tube and tighten and lock the locking screws of the staples to the rod and or the locking caps/nuts to the tips or ends of the staples. Distraction implements may also be employed and provided which are adapted to travel along the carrier tube of the percutaneous delivery system and grab a staple, allowing for one stable to be selectively and carefully pulled to allow for distraction between adjacent and otherwise aligned yet spaced staples.

The provided staples for the stabilization described herein further include a staple pre-fixed at a spaced interval to a common connecting rod before insertion of those components into the working channel of the delivery tube. In one embodiment, the locking screw component serves to secure the staple(s) to the connecting rod, acting through a camming mechanism which directs a locking wedge in the head of the staple to press against and hold the staple in place on the connecting rod. Also, the staple(s) can be fixed to the rod after insertion into the working channel, the latter being accomplished by the locking wedge and laterally directed small locking screw facing the working end of the working channel of the carrier tube so that the physician can lock the staples to the rod, by turning the locking screws, thereby camming the locking wedge to the rod, after the components are in place about the patient's processes.

BRIEF DESCRIPTION OF THE DRAWINGS

FIGS. 1 (A through F) are side and top elevational views of staples that are pre- and post-fixation tightenable, including a locking cap (FIG. 1E, by itself) in accordance with the invention;

DETAILED DESCRIPTION OF THE PREFERRED EMBODIMENTS, THE INVENTION AND THE DRAWINGS

Description will now be given of the invention with reference to the attached FIGS. 1-14. It should be understood that these figures are exemplary in nature and in no way serve to limit the scope of the invention as the invention will be defined by the attached claims, as interpreted by the Courts. The teachings, specification and drawings of U.S. provisional patent application Ser. No. 60/876,946, filed Dec. 22, 2006 and U.S. non provisional patent application Ser. No. 11/650,096 filed Jan. 5, 2007, based on U.S. provisional patent application No. 60/756,711, filed Jan. 5, 2006 are incorporated herein.

The purposes of the inventive staples and the stapler device (in the preferred embodiment a clamp in the nature of a pair of specially designed forceps or pliers) are mainly two-fold. First, it is to provide for spine stabilization via spinous process immobilization via a percutaneous approach. Second, it is to provide for spine distraction via interspinous process distraction using a percutaneous approach. The devices taught herein for accomplishing these desired goals are the preferred embodiments and method currently contemplated by the inventor for the devices and the method but, of course, other equivalents of the structure and the methods taught herein are intended by the inventor to be within the scope of the issued patent, as the claims are interpreted by the Courts.

Figure 1A:
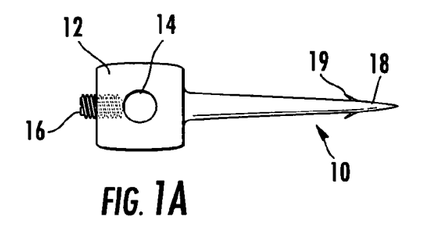
Figure 1B:
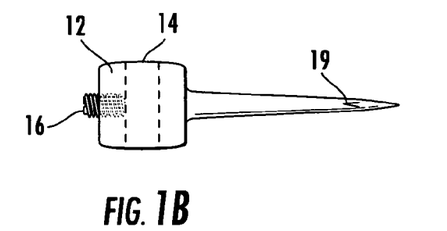
Figure 1C:
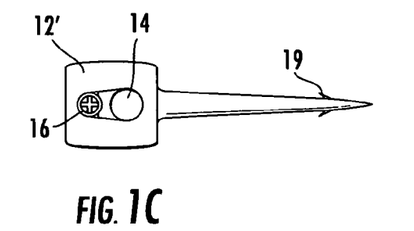
Figure 1D:
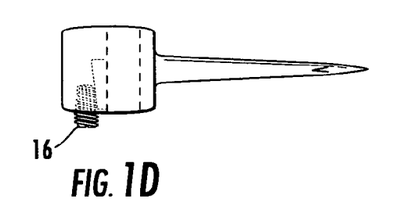
Figure 1E:
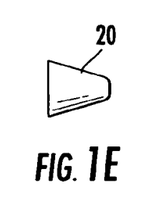
Figure 1F:
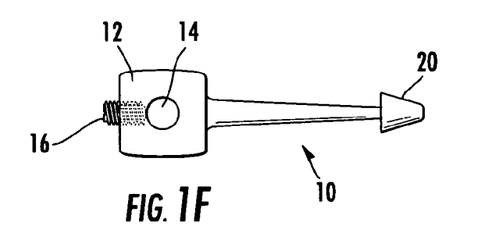
Figures 2, 3A, 3B:
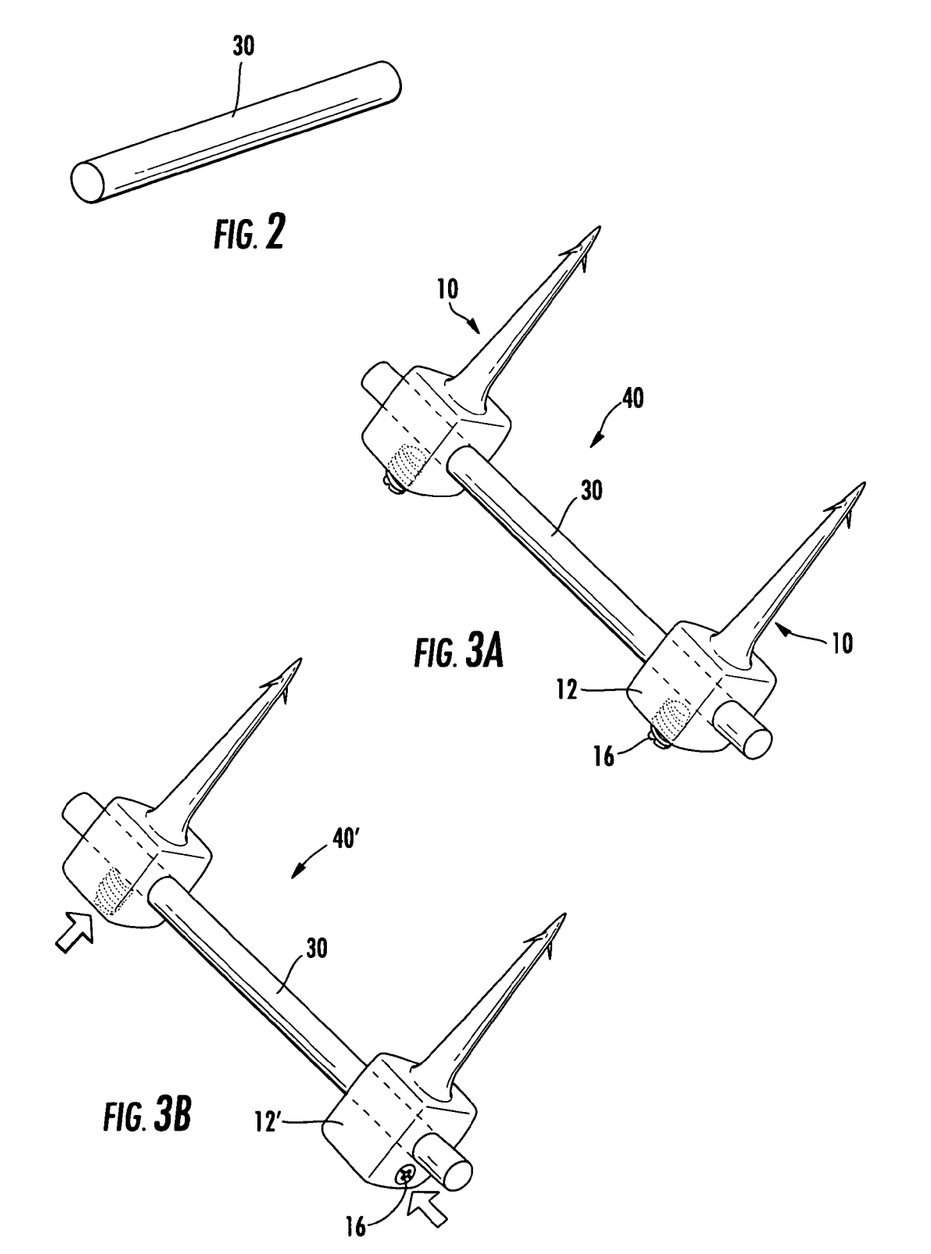
FIG. 2 is a side elevational view of a simple cylindrical connecting rod in accordance with the present invention.
FIGS. 3A and 3B are perspective views of two staples on the connecting rod (both the pre-fixed and post-fixed staples) in accordance with the invention.

The fundamental components of the inventive system include one or more staples 10 and a common fixation or connecting rod 30, shown in FIGS. 1 and 2. Staples 10 come in two similar currently preferred embodiments: the first—enabling pre-fixation tightening i.e. tightening before the device is located at the site of the patient's processes and the other, the second preferred embodiment of the staples, allows for and enables post-fixation tightening of the staples to the common fixation connecting rod. FIGS. 1A-B depict top and side views of the pre-fixation tightenable staple(s) 10, having a block or square-like-shaped head 12 with a central bore or working channel 14 passing through the head 12 of the staple. The bottom of the head 12 of the staple is preferably relatively large and flat to sit upon one portion of the spinal process sought to be immobilized. It is large in comparison to the pointed shaft of the staple and ensures that the staple does not pass through the spinal process but, rather, the head end of the staple will project out of the process and prevent complete passage of the staple through the process. The fixation or connecting rod 30 is preferably cylindrical in shape, i.e., circular in cross section and is of a suitable dimension to pass through the working channels 14 of the heads 12 of the staples 10. Other shapes of the connecting rod and the working channel of the staples could be employed, for example, square, oval, rectangular, etc. The staples can be adjusted to the proper spacing between them, by first sliding the staples along the length of the fixation or connecting rod 30.

The physician will determine the appropriate length of the rod, the size or length of the staples and the spacing between staples dependent upon the processes to be secured and/or distracted and the patient's needs. Of course, preliminary X-ray or other testing/probing and analysis will be performed by the physician before the stabilization system is employed. The entire procedure for implantation is intended to fully conform to acceptable and standard medical procedures and safeguards. However, as taught herein, a new device will be employed for use in the patient but still based on acceptable standards of care and procedure. The cylindrical connecting rod, staples, stabilizing plate and locking caps—indeed, all of the components intended to be used and installed into the patient for stabilization are expected to be made from quality titanium alloys or other medically acceptable and implantable materials and compositions, all well-known in the art.

Connecting rod 30 (FIG. 2) is adapted to slidably pass through the channels 14 or bores of the heads 12 of the staples 10 or stated another way, the staples are adapted to initially slide along the connecting rod 30 to their desired spacing. Then, in the post-fixation mode, a locking screw 16 is turned to secure the staple to the location on the connecting rod 30. The locking screw 16 is provided through a small bore in the head 12 of the staple, in communication with the working channel 14 of the staple. When the staples are suitably positioned on the connecting rod 30 and the locking screw is screwed clockwise through the small bore of the head of the staple, with the leading tip of the locking screw extending into the working channel 14 of the head of the staple, the further tightening of the locking screw 16 mechanically secures the staple 10 to the rod 30, at the desired location.

Each staple 10 is provided with a length of shank and at its end opposite to its head with a pointed tip or end 18 preferably having one or more small, laterally-extending barbs 19. Pointed tip or end 18 of the staples are intended to facilitate and allow staple 10 to easily penetrate the vertebrae while barbs 19 are provided to ensure that, once affixed to a vertebra, the staples 10 remain in relative position and orientation, i.e., the barbs, by coming into contact with surrounding bone, muscle or tissue minimize the staple's tendency to move, become loose, back out, or fall out/off.

A stabilizing plate 42, in the preferred form, an oval-shaped, flat top and bottom surface, with a curved outside wall on its ends, washer like device is placed over the tips of the shanks of the staples and the device then held together by locking screws or caps, extending over the tips 18 of the staples. On one side of the processes of the patient will be the heads 12 of the staples 10 and the connecting rod 30 while on the other side of the processes of the patient, the stabilizing plate 42 and the locking caps 20 will be located, thereby immobilizing the spinous processes.

To further secure the staples in situ, locking caps or nuts 20 are placed over the pointed tips or ends 18 of the staples to keep the staples from backing out. The locking caps 20 preferably have a smooth outside surface and tip, and cover and grasp the pointed ends of the staples. The locking caps preferably taper away from their openings, i.e., they taper toward their closed ends. The interior channel of the outside-tapered caps preferably is similarly tapered so that when a tip of a staple is forced by compression into the locking cap, the locking cap secures the tip of the staple within and prevents accidental backing out of the staple from the locking cap. The locking cap is frictionally secured to the pointed tip of the staple when the tip end of the staple is compressed into the locking cap.

In an alternative embodiment, the very tips of the pointed ends of the staple can be provided with exterior screw threads which will mate with the internally threaded screw threads of the locking caps or nuts. The locking caps can be internally threaded and mate with the pointed ends of the staples The length of the locking caps, its interior dimensions and degree of taper and the depth, slope, and other parameters of the interior bore or channel of the locking cap is determined by the tip of the staple so that they mate upon compressing the two components toward one another and the tip of the staple is held by the locking cap. The desired object being sufficient gripping of the cap on the tip of the staple to ensure that the locking cap or nut is, when secured to the tip of the staple, held there and will not unintentionally fall off.

The inside of the locking caps, in the preferred embodiment, would be a tapered conical cavity, adapted to mate with and frictionally hold onto the pointed tip of the staple so that when secured, the locking cap or nut will not accidentally be dislodged. The one way push-on aspect of this version of the locking cap has obvious mechanical, time, and other advantages especially important where complicated procedures in a small space are required. The locking caps can be secured, welded, mechanically secured to or otherwise affixed to the stabilizing plate 42, as shown in FIG. 4B.

The post-fixation tightenable staple is shown in FIGS. 1C and 1D having substantially the same elements as the pre-fixation staple, however staple head 12' in the post-fixation staple has a tapered locking screw 16 that screws into a side face of the staple head 12 rather than into a bore located in the rear face. This side face is intended to be facing the physician when the staple is installed so that he can easily adjust the location of the staple 10 on the connecting rod 30 and then turn the locking screw 16 of the head 12 of the staple 10 to adjust the spacing of the staples in situ. An enlarged view of the post-fixation tightenable staple is shown in FIG. 6. Here, the locking screw 16 does not tighten directly against the connecting rod 30 (as in the other embodiment) when the connecting rod is inserted through the bore 14 of the head of the staple but, rather, the contact made by the increasing diameter of the threads of the locking screw, as it is screwed into the side face of the head of the staple (through a small bore) pushes against and cams a locking wedge 17 to move the wedge 17 laterally against the connecting rod, thereby to tighten the staple to the connecting rod 30. This is best seen in FIG. 1D. Preferably, the rear or back end of the wedge is appropriately shaped (provided with separated threads or grooves, like a flat gear) which mate with the screw threads of the locking screw) to allow the threads of the locking screw, when the screw is turned, to slide the wedge which causes its acting surface to laterally engage the curved surface of the cylindrical rod. The acting surface of the wedge (the side which contacts the cylindrical rod) can be curved so that the wedge will mate with and tighten and grip around the curved surface of the cylindrical rod 30, as the screw is turned. The locking wedge, moved or cammed by the turning of the screw which acts on the back surface of the wedge, ensures a greater contact and securement of the staple at the precise location desired of the cylindrical rod 30. The curved surface of the wedge can also be slightly roughened or provided with a non-slip surface to ensure that the staple is located where it is desired or the connecting rod 30 and to also ensure against or minimize the tendency of the staple to rotate about the cylindrical connecting rod. The locking screw is secured within the head of the staple by a short partial segment of screw threads which mate with the screw threads of the screw, at and near the outside surface of the working channel. Alternatively, the mere capture of the screw in a bore and by the back surface of the locking wedge, coupled with the limited space in the working channel, can form a mechanical interlock between the locking screw, the camming wedge and head of the staple so that no additional threads need be machined into the head of the staple.

Figure 5:
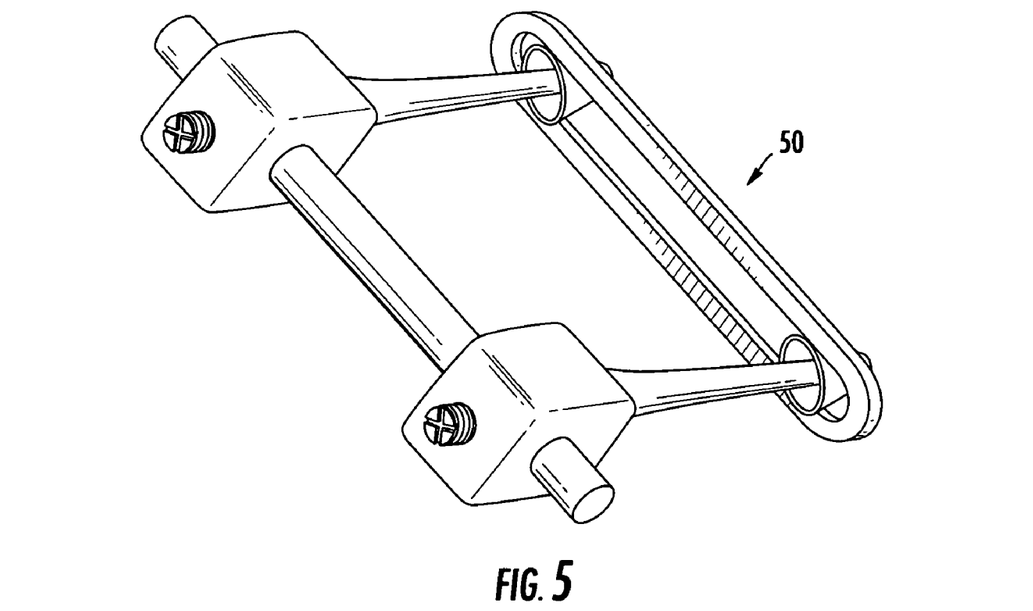
FIG. 5 is a perspective view of the entire construct of staples, connecting rod, locking caps, and stabilizing plate in accordance with the invention.
Figure 6A:
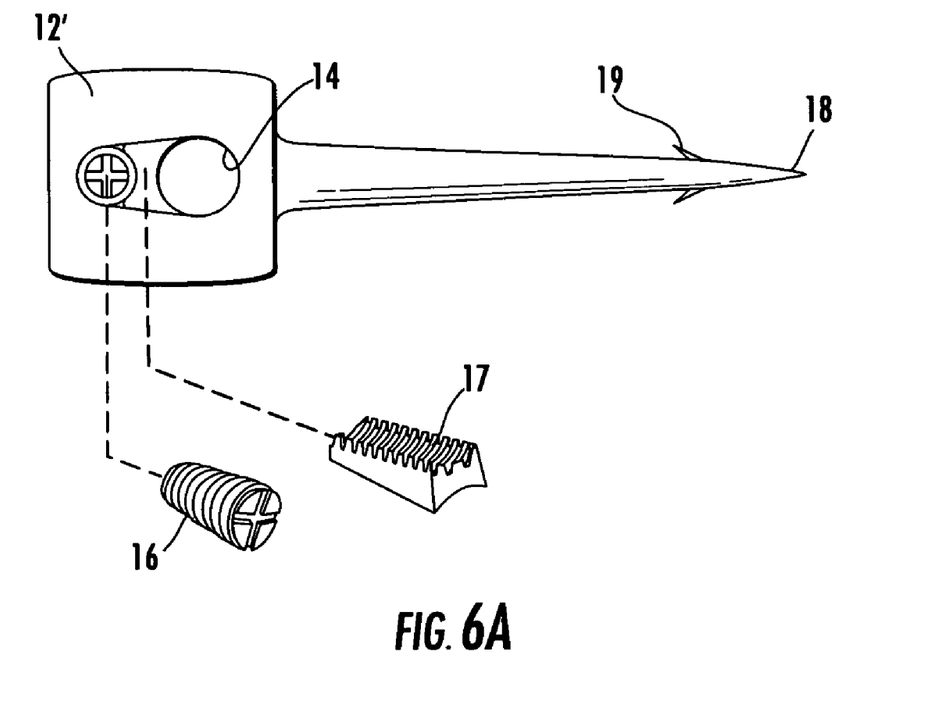
FIGS. 6A and 6B are enlarged, in comparison to FIGS. 1 through 5, side and top cross-sectional and partially exploded views of a post-fixed staple with locking wedge and locking screw in accordance with the present invention. In this application, pre- and post-fixation refers to the time when the physician secures the staples in place to the connecting rod and whether that is done before insertion of the construct into the patient or after the halves of the construct are inserted into the patient.
Figure 6B:
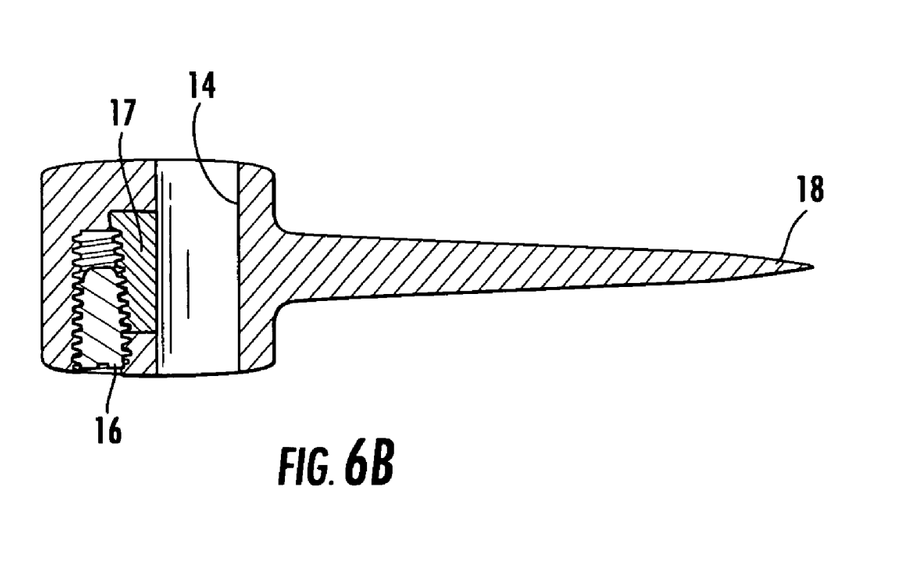

FIG. 3A and FIG. 5 show the pre-fixation tightenable staples secured to a cylindrical rod 30 as one half 40 of the overall construct 50, by use of the locking screw shown in FIG. 1B while FIG. 3B shows the post-fixation tightenable staples secured to cylindrical rod 30, as a construct 40', using the staples shown in FIGS. 1C, 1D, and FIG. 6A and FIG. 6B.

Figure 4A:
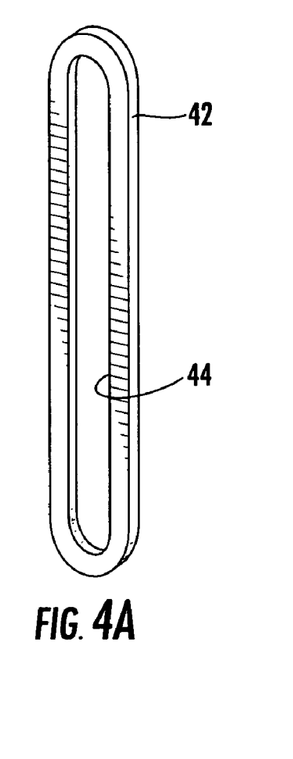
FIGS. 4A and 4B are perspective views of a stabilizing plate and locking, interiorly tapered, caps or locking nuts, in accordance with one aspect of the present invention. The locking caps or nuts are frictionally held onto the tips of the staples, much like, in shape and interior channel tapering, an electrician's wire insulation cap.
Figure 4B:
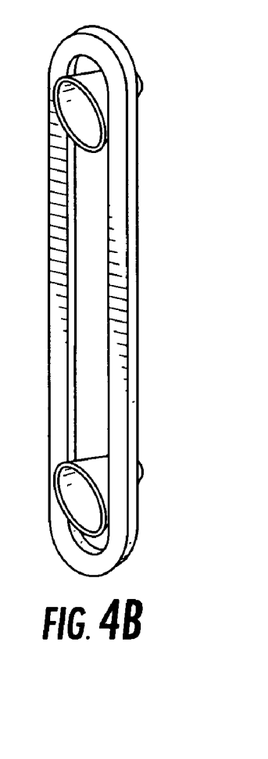

Another fundamental component of the inventive system is shown in FIGS. 4A and 4B, along with FIG. 5: A stabilizing plate 42 is depicted which is basically an apertured oval piece of stiff material (preferably metal), with flat top and bottom edges. Stabilizing plate 42 has a smooth outer side wall that defines an oval shape and an inner side wall that defines an oval aperture 44. Basically the stabilizing plate 42 resembles an oval shaped washer. The stabilizing plate 42 is provided with an open, oval-shaped aperture or center 44 into which the ends or tips of the staples project after they have been suitably located. The tips of the staples are small enough to pass through the oval-shaped aperture or center 44 and, yet, the heads of the staples and the locking caps are either secured to the stabilizing plate or can be located on the top of the plate and too big to pass through the central aperture 44. The flat bottom of the stabilizing plate 42 serves to provide a surface against the processes which when the tightening pressure of the staples are forced into the locking caps acts to maintain the processes under compression by the head of the staples being held on one side of the processes with their tips held on the other side within the locking caps. This immobilizes the vertebrae through which the staples pass. The stabilizing plate 42 rests against the spinous processes on the opposite side from the staples' heads 12 and their initial points of entry into the vertabrae. The entire staples/cylindrical rod/stabilizing plate and connecting or locking caps or nuts of construct 50 is shown in FIG. 5 (the spinous process is not shown for ease of illustration). As should be readily apparent, the tips of the staples reach and at least partially pass through the stabilizing plate and are gripped by the locking caps and, yet, the locking caps cannot separate from or pass through the center aperture 44 of the stabilizing plate 42. Rather, the base of the locking caps are either flush on the flat back of the stabilizing plate or the caps are secured to the plate. In one preferred embodiment, the diameter or outside dimension of the locking caps are sufficient to ensure that they bear against the back, flat surface of the stabilizing plate so that with the locking caps held by friction on the tips of the staples, the stabilizing plate is drawn toward and held in place by the mechanical cooperation of the heads of the staples on one side of the processes, the staples passing through the processes, with the stabilizing plate and locking caps on the tips of the staples on the other side of the processes. When installed appropriately and by a medical professional, this construct should immobilize the processes.

Figure 7A:
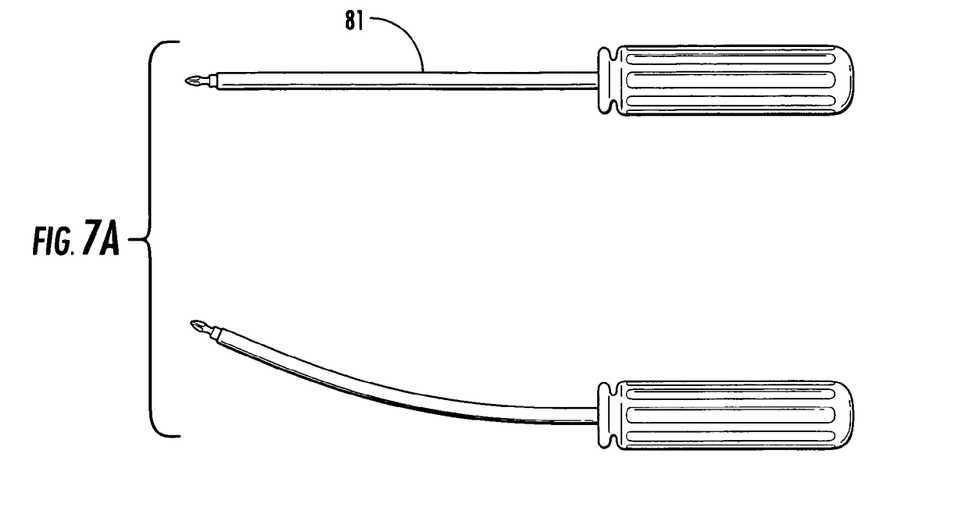
FIGS. 7A and 7B are side elevational drawings of various tools such as screwdrivers and staple graspers to be used percutaneously in accordance with the present invention.
Figure 7B:
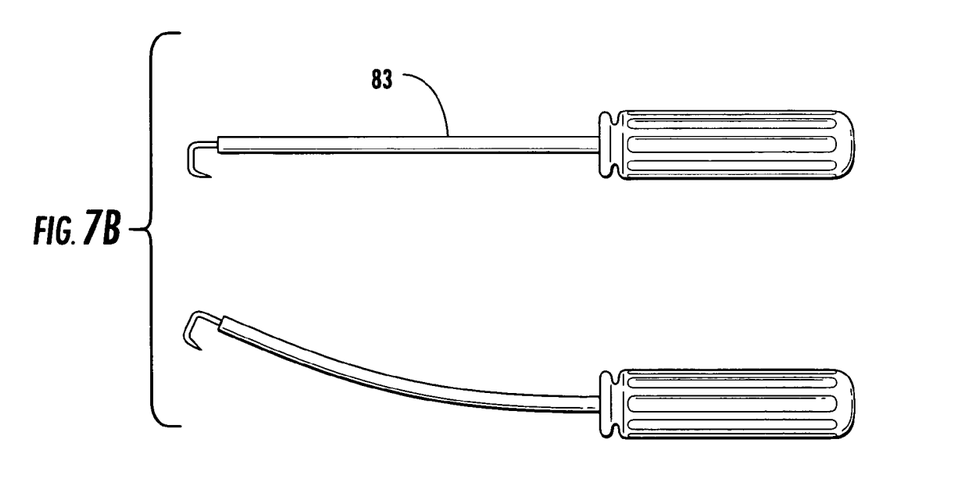

FIGS. 7A and 7B, show two examples of each of a straight and a curved implement/tool 81, for use with tightening and untightening (when adjustment along the cylindrical rod is required) the locking screws 16 in the head 12 of the stables 10 to secure, either pre- or post-insertion, the heads of the staples onto the cylindrical rod 30. FIG. 7B shows two versions (straight and curved) of a tool 83 for grasping and shifting the position of the staples in situ, for adjusting the location of the staples on the connecting rod.

Figure 8A:
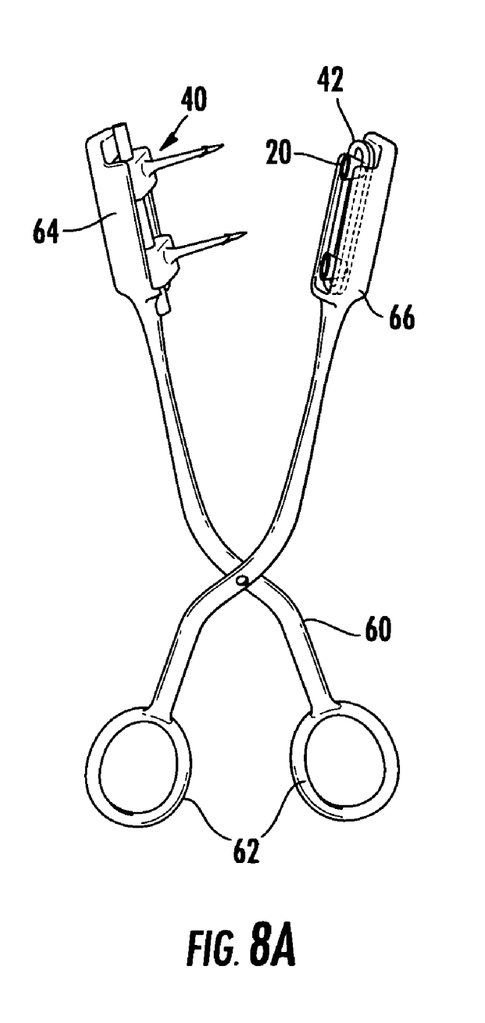
FIG. 8A and FIG. 8B are side elevational views of a carrier/compressor in the form of a clamp or pair of pliers, both loaded with the components, ready for use with a patient and then (FIG. 8B) empty after the construct of the staples, connecting rod, stabilizing plate and locking caps are inserted into a patient, all in accordance with the present invention. In the "loaded" view (FIG. 8A), the mechanical construct of staples and connecting rod (one half of the construct) are shown on one side of the hinged forceps or medical pliers-like device with the stabilizing plate and locking caps (the other half of the construct) on the other side of the forceps/pliers.
Figure 8B:
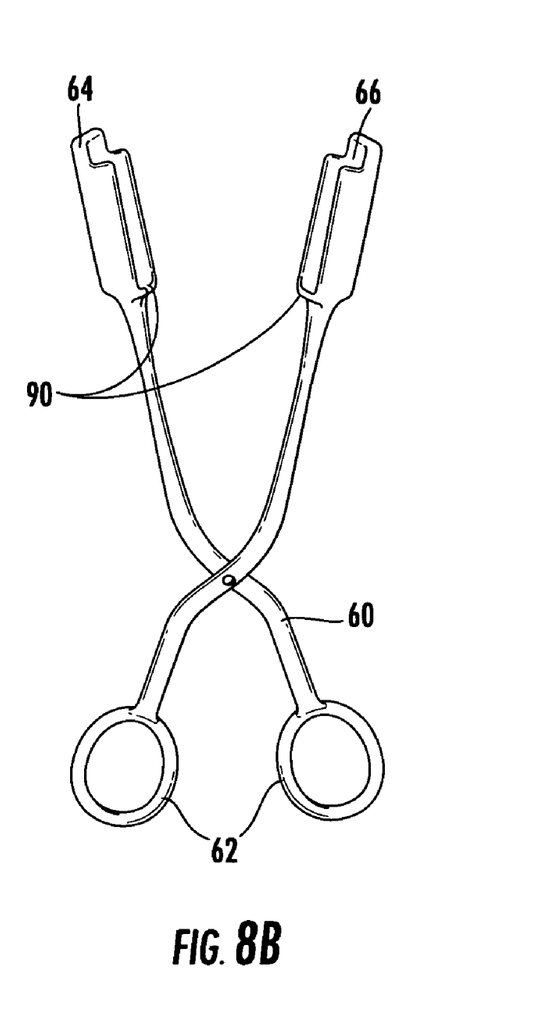
Figure 9A:
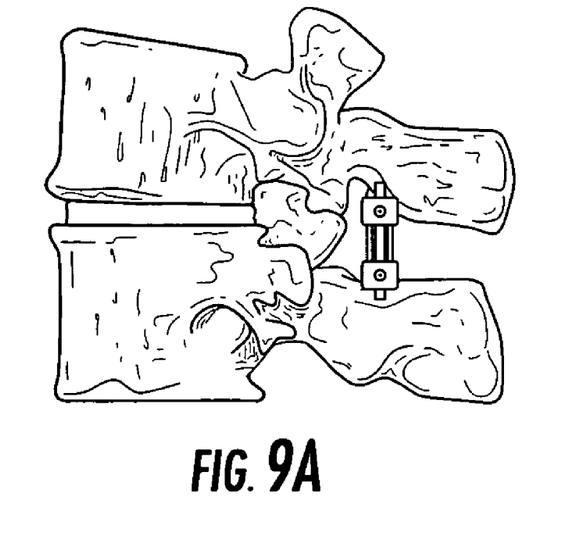
FIGS. 9A through 9D show various views of the inventive staples, connecting rod, stabilizing plate and locking caps or screw nuts being used as inter- and intra-spinous lumbar implants in accordance with the present invention. Some of the bone may appear removed for ease of illustration.
Figure 9B:
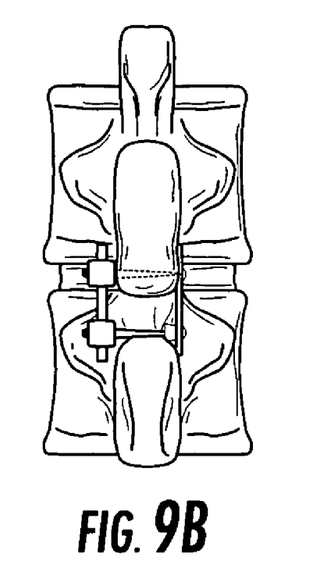
Figure 9C:
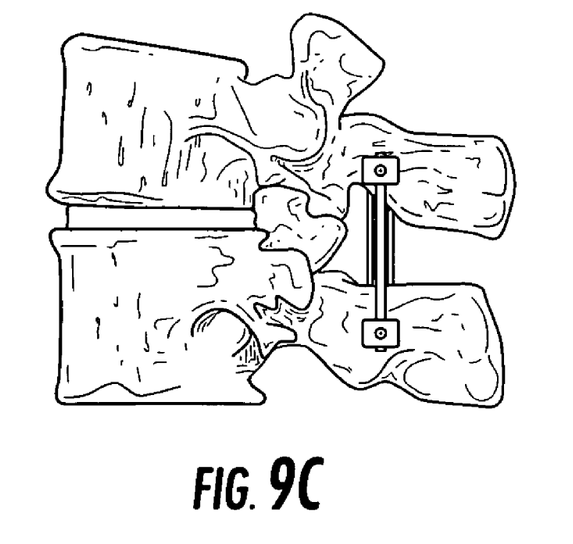
Figure 9D:
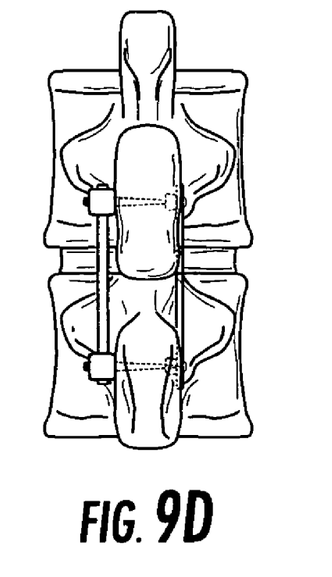

Construct 50 (See FIG. 5) is insertible and capable of being assembled together by use of a carrier, a forceps or pliers-like clamp 60 as best shown in FIGS. 8A and 8B. Clamp 60 includes finger-gripping handles 62 with finger holes to facilitate manual manipulation (as would a conventional clamp) and is hinged at a central pivot point. It has two arms and associated ends which are specifically adapted and designed to accommodate the staples and cylindrical rod, on one end of the first lever arm of the clamp, with the stabilizing plate and locking caps, on the other end of the second lever arm of the clamp. At the distal end of each arm of the clamp (distal in terms of the end of the clamp away from the finger grips) clamp 60 has a first end 64 into which is disposed (in this embodiment) a pair of staples 10 and a cylindrical rod 30 (all pre-secured together with the staples suitably spaced and secured to the cylindrical rod by the locking screws 16 being tightened). A second distal end 66 on the other end of the lever arm of the clamp is shaped to accept the stabilizing plate 42 and the locking caps 20. In the alternate embodiment, the staples are not pre-fixed in location but, rather, they are placed on the connecting rod at initial presumed correct locations but the final adjustment of spacing is performed by the physician by one or more of the laterally extending screws 16 and the locking wedge as shown in the embodiment depicted in FIGS. 1C; 1D; 3B and 6A and B.

The ends 64 ad 66 of the lever arms of the clamp 60 are preferably provided with a pair of opposed, upwardly extending and somewhat resilient flanges, extending along a length of the ends, and capable of gripping and only slidably releasing the respective segments of the construct 50. That is to say, end 64 has a pair of upwardly extending, opposed flanges which resilient grab and hold the heads 12 of the staples 10 with the cylindrical connecting rod 30 holding the staples in relative alignment. The other end of the clamp 66 is adapted, again, preferably with a pair of opposed, upwardly extending and resilient flanges, to hold the stabilizing plate 42 and locking caps 20 with the locking caps precisely located and held by the stabilizing plate or by either being secured within a channel of the stabilizing plate or by being secured into recesses in the end 66 of the clamp. Alternatively, the locking caps can be simply spaced apart the distance intended for the spacing of the tips of the staples and the frictional engagement of the tips into the locking caps will hold the caps in place. The respective "halves" of the construct 50 will not easily fall out of their respective ends of the clamp because of a shoulder or overhang of the flanges over the edges of the heads of the staples and the outer edge of the stabilizing plate. The outward resiliency of the flanges allow for easy loading of the clamp with the components but does not allow accidental removal of the components. When the clamp, with the halves of the construct 50 precisely located in position about the processes of the patient, the physician will squeeze the finger holes together and the clamp, functioning like a pair of pliers will bring the respective halves of the construct toward one another. With the leading and sharp tips of the staples piercing the processes/bone and then entering the openings of the tapered interior channel of the locking caps, with the stabilizing plate serving to equalize and spread the compressive pressure of the construct along its length, the halves are secured together—the tips of the staples are captured within the locking caps by further tightening on the clamp, and then the construct, held together and in place through the processes, is released from the clamp. This is done by pulling the clamp laterally, i.e., the far open ends at the distal ends of the lever arms of the clamp allow the staples and cylindrical rod, along with the stabilizing plate and locking caps, to glide and slide laterally out of the clamp, thereby separating the construct from the clamp, leaving the construct in place in the processes. The clamp can then be removed from the patient.

Figure 14:
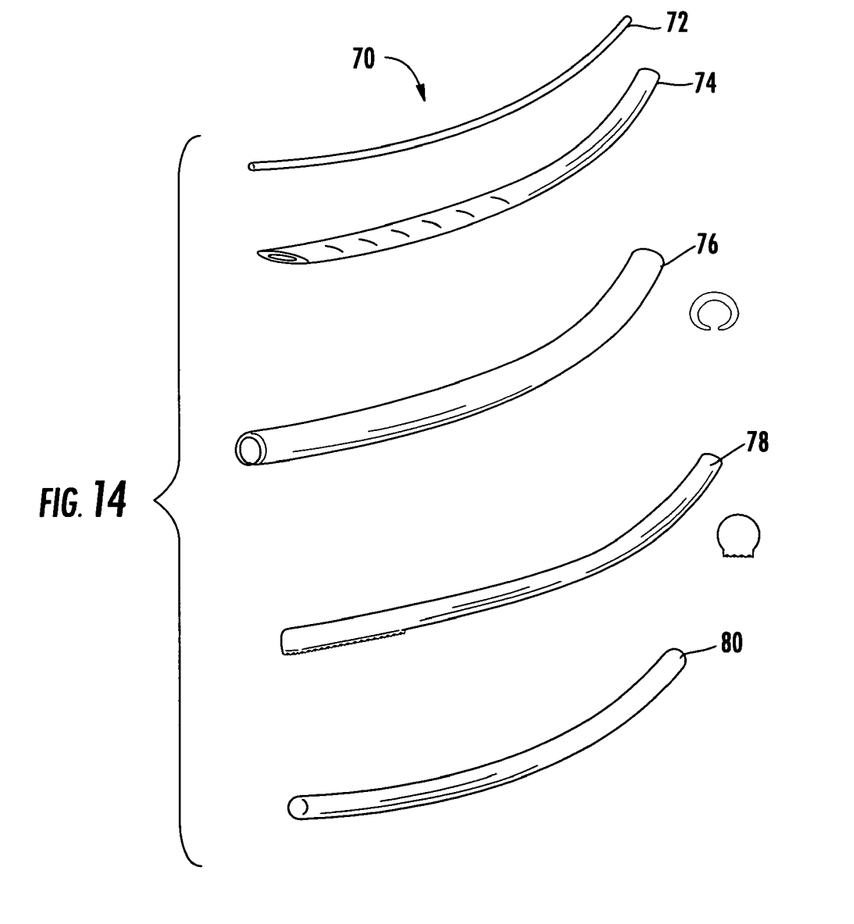
FIG. 14 depicts an inventive delivery system that allows the inventive staples, connecting rod, stabilizing plate and locking caps, as constructs, to be introduced into the body in a percutaneous manner, substantially as shown by use of the implements described in the prior mentioned non-provisional U.S. patent application of the same inventor.

The carrier clamp may be introduced percutaneously via a percutaneous tube delivery system. One such system was also invented by the instant inventor. The basics of that inventive tubular delivery system 70 is shown in FIG. 14 and is more fully described and shown in the aforementioned non-provisional U.S. patent application Ser. No. 11/650,096 filed Jan. 5, 2007. Those teachings are entirely incorporated by reference herein. In brief summary, however, a trocar or solid, cylindrical in cross section wire-like tool 72 has a sharp leading tip and is typically solid like a wire rod, yet preferably curved. The trocar 72 may be embodied as part of a cannula, such as a cannular trocar. After the trocar is introduced into the patient and forms a small bore or channel through tissue, a dilator 74 is typically used to create a wider channel than the one made by the trocar 72. Dilator 74 typically is also cylindrical in cross section, of greater outside diameter than the trocar and has a hollow central opening along its length with an interior diameter slightly greater than the outside diameter of the trocar so that the dilator can slide over the first inserted and in-place trocar. This will widen the channel or bore made in the patient. Then the guide wire or trocar 72 is removed leaving the dilator 74 in place. Delivery or carrier tube 76 is also typically hollow, thin walled, and preferably shaped (to conform to the curvature of the trocar and the dilator) and allows other instruments, such as endoscopes, to be introduced to facilitate viewing the condition of tissue or the like. The carrier tube 76, is slid over the dilator (its interior diameter is slightly larger than the outside diameter of the dilator) and then the dilator is removed leaving the delivery tube 76 in place. The delivery tube 76 is substantially hollow and has a longitudinal or lengthwise slit to allow for another implement or tool to be slid within it and to allow that newly introduced implement or tool 78 (a rasp) to project outward through the slit or at the distal end of the delivery/carrier tube, to accomplish a desired procedure/result. For example, the placement of the delivery or carrier tube 76 in situ allows entry of a decorticator, a rasp, a pushing instrument, a syringe, medication, or other substances, to be delivered to the region of interest, or to remove tissue, bone, or a specimen from the region of interest. In this embodiment, the carrier tube 76 can be used to allow for one arm of the clamp for installation of the stabilizing construct 50 or system. A second carrier tube 76 can be used for the other end of the arm of the clamp just as the first carrier tube was installed. A tool, like a rasp 78 (located at the distal end of the tool/implement) may be provided and is typically solid, and typically has a serrated working surface or distal edge at its distal end. The rasp 78 can slide within and slightly reciprocate in the channel of the carrier tube 76 to cause the desired effect, if needed, in one case, to abrade the surface of the tissue, bone, etc. A pusher rod can 80 be used to push medication, a liquid or other substance, such as a bone matrix or bone fusion substance to the region of interest, again, through the carrier tube 76. These tools and system are useful for the purposes set forth in the aforementioned US non-provisional patent application, filed Jan. 5, 2007. In addition, however, a similar system and set of tools can be used with the present stabilization construct 50 and to allow for the introduction of the clamp 60, with the halves of the stabilization construct pre-loaded thereon, so as to insert the halves into the patient and then clamp them together for installation about the processes sought to be immobilized.

With reference to the carrier clamp 60, the lever arms of the clamp, after loading them with the halves of the construct 50 can preferably be slid along carrier tubes 76 until the arms are in the precise and desired location, proximal to the processes sought to be stabilized. Once in location, the finger grips and arms of the clamp 60 are squeezed by the physician thereby having the tips of the staples pass through the processes and then through the stabilizing plate and into the locking caps. Various screwdrivers (and staple graspers) (see FIGS. 7A and 7B) can also selectively pass through the carrier tube(s) and can tighten and lock the locking screws for the staples where desired and/or adjust the staples onto the cylindrical rod (or grasp the staples for removal).

In operation, the inventive process and bone stabilization system is used as follows.

The patient is on the operating table in the prone position under general anesthesia or with local anesthesia and a lateral fluoroscopic image of the area of the spine of interest is obtained. Either a spinal stabilization (fusion) or a distraction may be performed by use of the invention. Of course, the physician is the expert to diagnose and advise the patient according to sound medical ethics and procedures.

When performing a stabilization, the desired distances of the processes, of the spinal column, of the bones, etc., are measured. If performing an intraspinous process stapling, the spot of the spinous process to be perforated is selected and then the spot in the adjacent spinous process selected and the distance between the two carefully measured. If performing interspinous process stabilization, the distance from the outer edge of the spinous process to that of the opposite outer edge adjacent spinous process is measured and then the distance from inner edge to inner edge is measured. This is clearly thought to be understood by those of ordinary skill in the art, namely surgeons dealing with the treatment of spinal columnar maladies. When distraction is intended, the distance from inner edge to inner edge of the respective processes are measured. The measurements help the physician determine the length of staple, the distance between staples, the size of the stabilizing plate, etc.

When performing an intra-spinous pre-fixing process stapling, the staples 10 are first set on the cylindrical rod 30 at the measured distance and the screws 16 in the heads 12 of the staples tightened to lock the staples onto the connecting rod at the set distance apart. The appropriate length of the stabilizing plate 42 is selected and the locking caps 20 are secured within the second arm of the clamp, also at the measured distance apart. The staples and connecting rod half of the construct is then loaded into the first lever arm of the clamp 60 on side 64 (by either sliding the same into and through the free/open end of the first arm of the clamp or by pushing against the resilient flanges to top load the half) and the stabilizing plate with the locking caps 20 are secured into the other side 66 of the opposed lever arm of the clamp 60. The halves of the construct 50 are press fit into the ends 64 and 66 of the lever arms of the clamp by forcing the halves down into the clamp and the halves, i.e., the heads of the staples and the stabilizing plate bend outwardly the inwardly biased resilient flanges. This captures the halves of the construct 50 in the ends of the lever arms of the clamp 60. A shoulder or stop 90 located on the proximal ends of the lever arms of the clamp 60 serve to prevent the halves of the construct 50 from sliding all the way through the clamp (if the halves of the construct are loaded into the clamp through the open ends).

Carrier tubes 76 are then inserted (as a step in the process described above) percutaneously along the spinous processes, bilaterally under fluoroscopic guidance. Clamp 60 is then inserted through the tubes (the opening grooves of the tubes are located against the spinous processes) and positioned in the desired location, also via fluoroscopy. Clamp 60 is then tightened by hand squeezing the finger holes 62, like a pair of forceps or pliers, bringing the tips 18 of the staples 10 through the spinous processes and into the opposed but appropriately spaced locking caps 20. The tips of the staples first pass through the stabilizing plate, before they are frictionally captured within the locking caps. The barbs 19 of the tips of the staples serve to ensure that the locking caps secure the construct and ensure that the staples do not move about, after location and placement. With the tips of the staples captured within the locking caps, the arms of the clamp can be proximally retracted out through the carrier tubes, leaving behind the construct in the processes. As mentioned, with the construct in location and secured into the locking caps, through the stabilizing plate, the arms of the clamp can be withdrawn from the patient and the construct will remain in place as the halves, now joined, can easily glide and slide out of the open and free ends of the clamp 60 as the clamp is withdrawn. Clamp 60 is fully removed with the construct 50 left in place. The heads of the staples 12, secured to the cylindrical rod 30, will be on one side of the processes while the stabilizing plate 42, with locking caps 20, will be located on the other side of the processes, with the construct held together by the gripping of the tips of the staples inside the opening of the locking caps. The heads of the staples, in cooperation with the stabilizing plate, fix the spinous processes.

In an alternate embodiment a second stabilizing plate can be used on the side of the construct with the heads of the staples and the cylindrical connecting rod. In this embodiment, the second stabilizing plate is held beneath the heads of the staples and against the processes, much like the first stabilizing plate on the other side of the processes.

When performing an interspinous process stapling, the procedure is basically the same, but four staples may be used along the superior and inferior edges of the spinous processes. The appropriate distances are measured and the staples 10 are secured on the one or more cylindrical rods 30 at the desired distances. The corresponding stabilizing plate and the mating locking caps are likewise measured and prepared. This new set of components are loaded onto a suitably dimensioned clamp 60. After the working channel of carrier tube 76 has been placed, clamp 60 is passed into the channel and under fluoroscopic guidance, the staples are positioned and then the stabilizing plate(s) and its secured number of locking caps are clamped together.

When performing an inter-spinous distraction, the distance between the two selected spinous processes is measured fluoroscopically and the staples 10 are placed on the appropriate length connecting rod 30 and the locking screws 16 pretightened to ensure that the spacing is maintained. The locking caps 20 are appropriately placed and spaced on the stabilizing plate 42 at the same distance apart as the tips of the staples. Clamp 60 is then loaded with the respective halves of the construct and its arms are located in the working channels of carrier tubes 76. When the halves are located and the location confirmed, the staples 10 are passed (by squeezing the clamp) into the opposed locking caps 20 with the tips of the staples first passing through the inter-spinous space and then through the stabilizing plate. The post-fixed staple is utilized proximally and then proximal screws are loosened and the staple grasping device (see FIG. 7B) is inserted around the proximal staple. Distraction is carried out to the desired distance. Then, the locking screw is tightened (using tool from FIG. 7A). Finally, the working channels 78 are removed.

In another embodiment, interspinous stabilization is provided through the percutaneous longitudinal curved working channel. As shown in FIG. 12A-12D, a set of various sized plates 160 can be made available. Each is provided with speculated inner surfaces 162 and one set is further provided with a center, upwardly extending post 164 comprised of a pair of legs which are slightly inwardly resilient at their bases (on the plate) such that when located in the patient, the tip or leading end of the post passes between the spinous processes. The sizing of the speculated plates allows for selective stabilizing of cervical, thoracic, or lumbar spinous processes. Correspondingly, a similar set of speculated plates with a central receiving hole are provided. The leading tip or end of the speculated plate is adapted to pass through the receiving hole of the opposed speculated plate and the resilience of the legs of the post 164 allows the post 164 of the plate 162 to be captured and held to the opposed speculated plate. They will, of course, be separated by the distance of the process held by the opposed speculated plates. For precise insertion and ease of installation, a similar clamp to that of clamp 60 can be used. The plate 160 with the post 164 and the opposed plate 160' with its receiving hole 166 are slid into the free open ends of the lever arms of the clamp. The clamp 200, with resilient flanges to hold the plates and end openings on the distal portion of the opposed arms of the clamp is introduced to the desired location through the working channel(s) of a system of tubes as shown in FIG. 14, via fluoroscopy. The clamp is then brought together and the plates brought toward one another by the squeezing action of the physician on the opposed finger holes of the clamp 200, acting about the central hinge of the device for compressive force. The opposed plates are secured to one another, i.e., the central post is captured by the outward bias of a suitable dimensioned and shaped recess in one of the legs around the edge of the aperture 166 in the opposed plate. The bending of the legs of the post, through the opening of the opposed plate and then the resilience of the legs and the interaction of the recess with the edge of the opening or aperture 166 maintains the plates in relative orientation and spacing. After securing the plates, the clamp is then slid out and the plates left in situ. After the procedure is completed the working channels are removed and the patient appropriately closed.

Figure 10A:
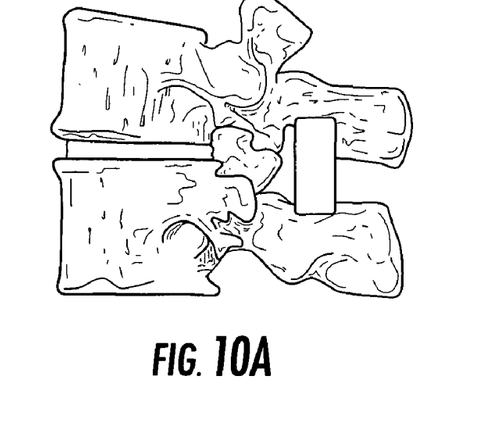
FIGS. 10A and 10B show alternative views of the usages of the components and devices, as shown in FIGS. 9A through 9D.
Figure 10B:
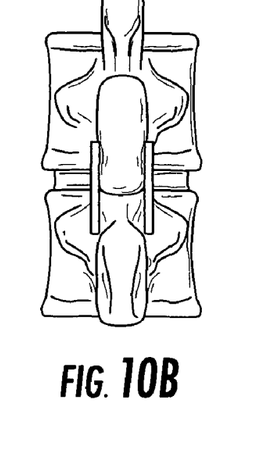
Figure 11A:
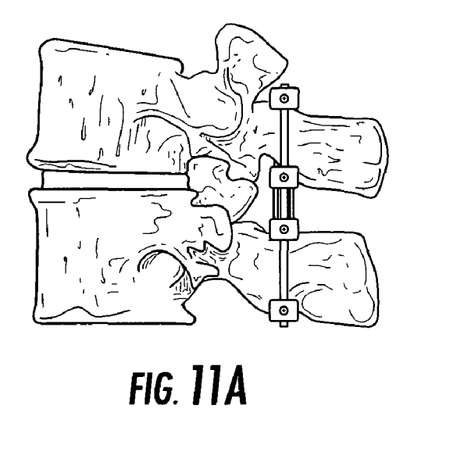
FIGS. 11A through 11C show various views of the inventive staples (four are in use in these examples), a single connecting rod, an opposing stabilizing plate and the locking caps or screw nuts being used as inter- and intra-spinous cervical implants in accordance with the present invention.
Figure 11B:
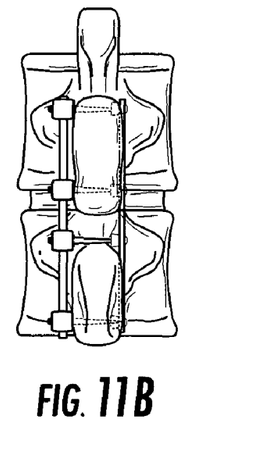
Figure 11C:
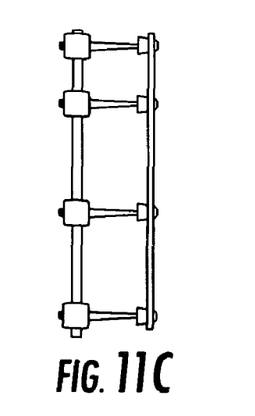
Figure 12A:
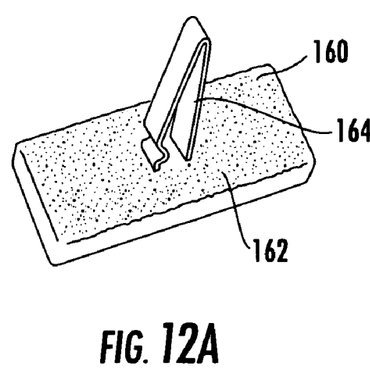
FIGS. 12A through 12D show perspective and side views of a speculated, i.e., roughened plate with an upwardly extending center post (comprised of inwardly resilient legs tapered toward the top of the post) and an attachable speculated nut plate, along with a clamp or pliers/forceps-like device, loaded with the mating and engagable, speculated plates in accordance another aspect of the present invention.
Figure 12B:
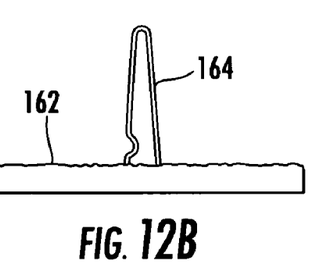
Figure 12C:
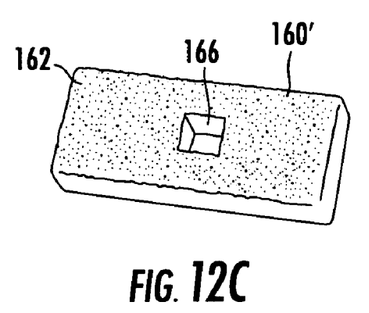
Figure 12D:
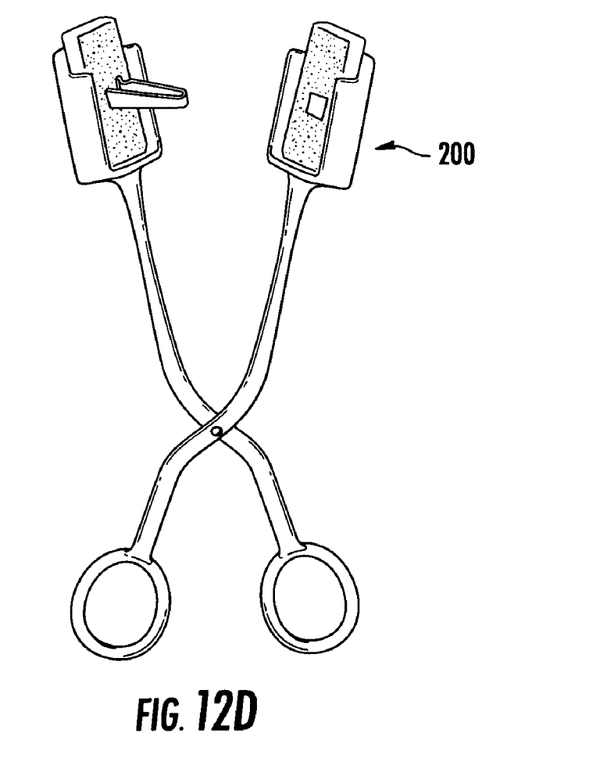
Figure 13A:
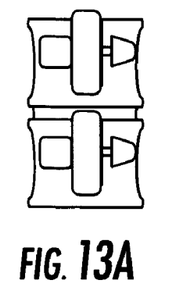
FIGS. 13A-13K show schematic views of various configurations of the inventive staples, connecting rods, stabilizing plates and locking caps, all in situ.
Figure 13B:
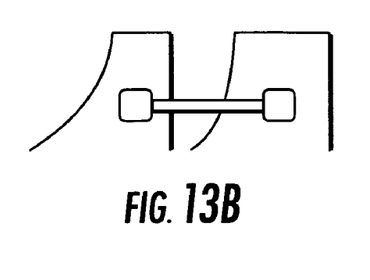
Figure 13C:
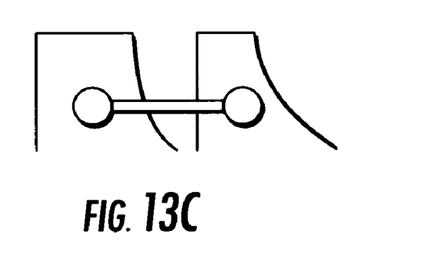
Figure 13D:
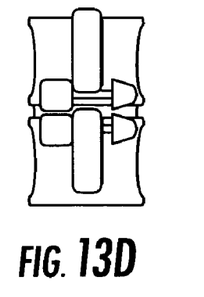
Figure 13E:
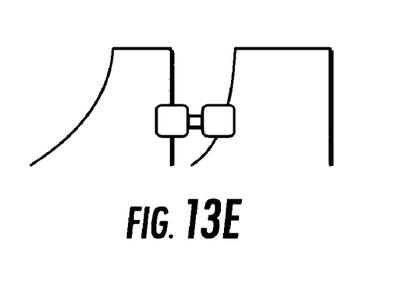
Figure 13F:
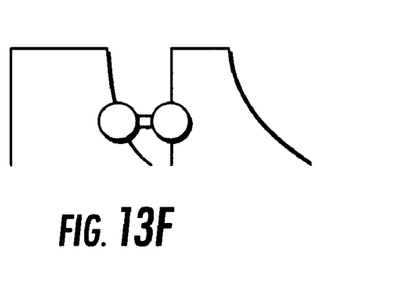
Figure 13G:
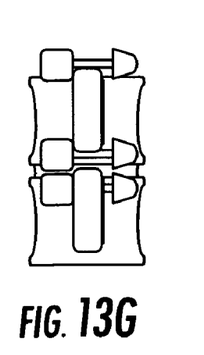
Figure 13H:
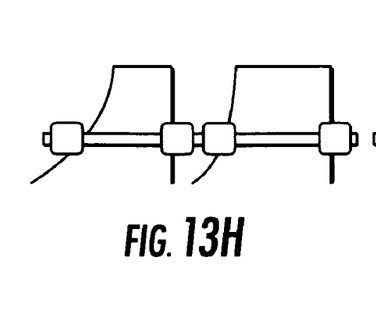
Figure 13I:
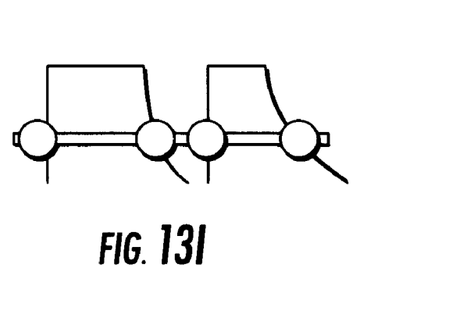
Figure 13J:
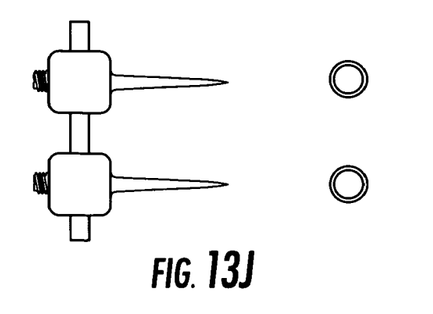
Figure 13K:
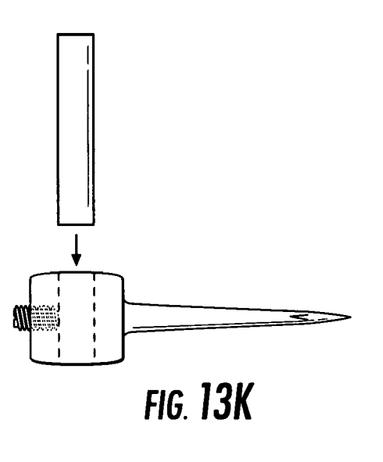

FIGS. 10A and 10B; 11A-11C; and FIGS. 13A-13I schematically illustrate and show how the stabilizing device, comprising staples, rods, stabilizing plate and locking caps can be used in interspinous and intraspinous procedures. Also, the speculated plates can be used, as well, in various procedures. The roughness or speculation on the surface of the plates enhances the "hold" of the plates to the various processes and ensures that the plates, when held together by the cooperation of the resilient post and the receiving hole, do not unnecessarily move from the desired location.

The invention is not limited to the above description. Various modifications that would be readily apparent to those of skill in the art are contemplated as falling within the scope of the invention.

I claim:

1. A spinous stabilization system comprising:
   a) a substantially rigid connecting rod, comprising a substantially circular cross-section;
   b) at least two staples adjustably spaced and secured along the length of said rod, each of said staples having a head end and a spinous process piercing tip;
   c) a stabilizing plate having opposed relatively flat surfaces; said stabilizing plate having a central opening for receipt therethrough of said piercing tips of said staples; and
   d) a locking cap for engagement with each of said piercing tips of said staples, when said staples pass through a spinous process and through said central opening of said stabilizing plate to secure said stabilizing plate to said staples and against said spinous process, and
   e) a laterally-directed locking screw and a camming wedge in the head of at least one of said staples, said locking screw and camming wedge mechanically operating such that rotation of said laterally directed locking screw in a first direction causes said camming wedge to move in a second direction thereby locking said staple to said connecting rod.

2. A spinous stabilization system as claimed in claim 1 wherein said head of said staples has a working channel shaped to the cross-sectional shape of said rod.

3. A spinous stabilization system as claimed in claim 1, further comprising a locking screw in each of said heads of said staples to secure said staples to said connecting rod.

4. A spinous stabilization system as claimed in claim 1 wherein the piercing tips of said staples are provided with at least one outwardly flared barbs.

5. A spinous stabilization system comprising:
   a) a connecting rod;
   b) at least two staples adjustably spaced and secured to said rod, each of said staples having a head end and a spinous process piercing tip;
   c) a stabilizing plate having opposed relatively flat surfaces; said stabilizing plate having a central opening for receipt therethrough of said tips of said staples;
   d) a locking cap for engagement with each of said piercing tips of said staples, when said staples pass through a spinous process and through said stabilizing plate, and where said locking caps are greater in dimension than said central opening of said stabilizing plate so that said locking caps cannot pass through said central opening; and
   e) a laterally-directed locking screw and a camming wedge in the head of at least one of said staples, wherein said camming wedge has a back surface mechanically coupled to said locking screw and a front surface shaped to hold said staple to said connecting rod.

6. A spinous stabilization system as claimed in claim 5 wherein each of said piercing tips of said staples is frictionally captured by one of said said locking cap.

7. A spinous stabilization system as claimed in claim 6 wherein each of said locking caps are provided with an internally tapered channel for capturing and securing the tip of said staple captured thereon.

8. A spinous stabilization system as claimed in claim 5 wherein said rod is substantially cylindrical.

9. A spinous stabilization system as claimed in claim 5 wherein said rod is substantially rigid.

10. A spinous stabilization system comprising:
a) a connecting rod;
b) at least two staples adjustably spaced and secured along the length of said rod, each of said staples having a head end and a spinous process piercing tip;
c) a stabilizing plate in the form of an oval-shaped, flat washer having opposed relatively flat surfaces; said stabilizing plate having a central opening large enough for receipt therethrough of said tips of said staples; and
d) a locking cap for engagement with each of said piercing tips of said staples, when said staples pass through a spinous process and through said stabilizing plate, wherein said locking caps are greater in dimension than said central opening of said stabilizing plate so that said locking caps cannot pass through said central opening of said stabilizing plate.

11. A spinous stabilization system as claimed in claim 10 wherein said rod is substantially cylindrical.

12. A spinous stabilization system as claimed in claim 10 wherein said rod is substantially rigid.

\* \* \* \* \*